United States Patent [19]

Shek

[11] Patent Number: 5,105,490
[45] Date of Patent: Apr. 21, 1992

[54] APPARATUS FOR SUPPORTING THE HUMAN BODY

[76] Inventor: Kwei C. Shek, 16 Fort Street, G/F., North Point, Hong Kong

[21] Appl. No.: 428,612

[22] Filed: Oct. 30, 1989

[30] Foreign Application Priority Data

Oct. 31, 1988 [CN] China .................. 88107558

[51] Int. Cl.$^5$ .......................................... A47C 27/00
[52] U.S. Cl. .......................................... 5/448; 5/468; 128/57
[58] Field of Search ............... 5/186 R, 188, 448, 461, 5/462, 464, 468; 600/9, 15; 297/382, 453; 128/57

[56] References Cited

U.S. PATENT DOCUMENTS

| | | | |
|---|---|---|---|
| 3,840,923 | 10/1974 | Bos ........................ | 5/461 X |
| 4,122,568 | 10/1978 | Bastos et al. ............... | 5/448 |
| 4,143,435 | 3/1979 | Masuda .................... | 600/9 X |
| 4,161,045 | 7/1979 | Regan ..................... | 5/464 |
| 4,169,466 | 10/1979 | Wong ...................... | 128/57 |
| 4,330,892 | 5/1982 | Fukushima ................. | 5/462 X |
| 4,509,219 | 4/1985 | Yagi ....................... | 5/448 X |
| 4,673,605 | 6/1987 | Sias et al. ................. | 5/464 X |
| 4,713,854 | 12/1987 | Graebe .................... | 5/448 X |
| 4,903,356 | 2/1990 | Morisaki .................. | 5/448 X |
| 4,924,542 | 5/1990 | Yamaguchi ................ | 5/448 X |
| 4,936,294 | 6/1990 | Chu ....................... | 128/57 |

FOREIGN PATENT DOCUMENTS

2323851 5/1973 Fed. Rep. of Germany ........ 128/57

Primary Examiner—Michael F. Trettel
Attorney, Agent, or Firm—Knobbe, Martens, Olson & Bear

[57] ABSTRACT

A support apparatus in the nature of a mattress comprises means defining an array of pressure points for the application of pressure to parts of a human body resting on the support member. The means defining the array of pressure points are connected together to form a layer which is covered by a cover. The pressure points are preferably defined by bead members and the support apparatus is advatangeously flexible. Additionally, a cushioning layer may be added beneath said layer to provide a restoring force delivering a somewhat gentler massaging effect at the pressure points.

2 Claims, 8 Drawing Sheets

APPARATUS FOR SUPPORTING THE HUMAN BODY

The present invention relates in general to a method of and an apparatus for supporting the human body and in particular to a massage apparatus which is adapted to serve as a mattress, pad or the like for producing massaging effect.

Conventionally, it has been believed that a pad or mattress having a soft feeling assures a sound sleep. The conventional mattress is made of extremely soft material, such as urethane foam rubber. However, such mattresses are so soft that the spinal cord of a user tends to bend downwardly during sleeping. Consequently, the weight of the user cannot be uniformly supported by the mattress. The user often feels pain in his shoulder, waist or spinal cord. On the other hand, some people believe that a mattress made of hard material assures a sound sleep. However, in practice, this type of mattress is not suitable for any person except youngsters, since it causes the upward curving of the spine and the stretching of muscles.

Accordingly, the ideal condition of a pad or mattress is soft to the touch but firm enough to uniformly distribute the user's weight.

However, previously proposed mattresses meeting these criteria are relatively bulky and heavy. In addition, they cannot be rolled up for easy storage and transportation and do not promote the respiration of skin of the user's body to prevent undesirable rises in body temperature.

In accordance with one aspect of the present invention, there is provided human body support apparatus comprising means defining an array of pressure points for the application of pressure to parts of the human body, means for connecting said first mentioned means to form a layer, and cover means for covering said layer.

The beads are preferably made of a relatively hard material, such as wood, plastic or rubber. The beads are preferably spherical, semispherical, oval, elongated or irregular in shape or a combination thereof. The beads are preferably disposed in orthogonal, diagonal or irregular array.

According to a first embodiment of the invention, each of the beads has a through hole whereby the beads are adapted to be linked up together by string or line means. The strings are made of a flexible and high tensile material such as thread, nylon or steel wire.

According to a second embodiment of the invention, the beads are secured to a sheet member fabricated of cloth, of nylon or other suitable materials.

As illustrated for the embodiment, a cover encloses the layer of beads, thus producing a clean and comfortable exterior for the mattress. This cover is preferably made of cloth, thin foam rubber, or leather. Additionally, cushioning may be placed under the layer of beads to provide a restoring force to said layer, thereby producing a cushioning effect. This cushioning is preferably made of a resilient material such as foam rubber.

The mattress or pad of the present invention may further be provided with magnetic devices such as magnets. The magnets are positioned between and among the beads and are disposed at the regions of the mattress which come into close contact with the body of the user.

The magnetic force generated from the magnets has a healing effect on users suffering from fatigue. It releases the user from pain in the spinal cord and waist and from stiffness in the shoulders.

A unitary layer of the beads uniformly supports the body of the user and produces massaging effects at various points of the body of the user.

The mattress or pad is characterized in that a lot of space is provided between the beads rendering the mattress or pad to have excellent ventilation. It allows the sweat which is formed to be effectively ventilated away so that the body is held at a suitable temperature.

In accordance with a further aspect of the invention there is provided a method for supporting a human body comprising the step of resting a part of the human body on or against a layer which defines an array of pressure points for the application of pressure to said part of the body.

Many other advantages and features of the present invention will become apparent to those skilled in the art upon making reference to the detailed description and the accompanying drawings in which preferred structural embodiments incorporating the principles of the present invention are shown only by way of illustration.

Figure 1:
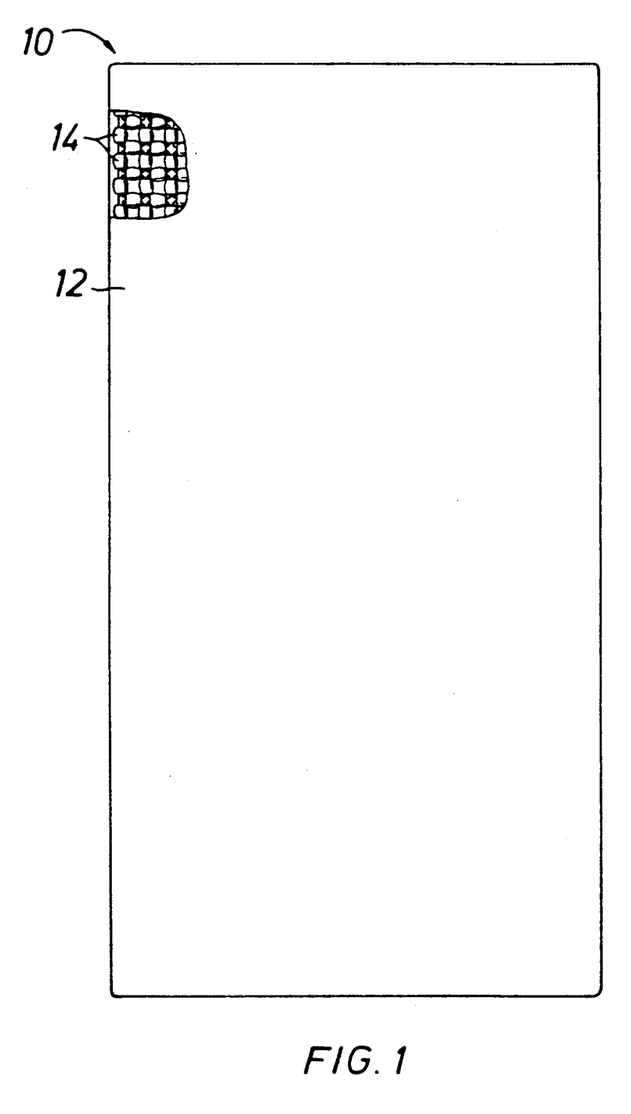
FIG. 1 is a plan view of a mattress or pad according to the present invention with a portion of the cover being cutaway showing the inner structure thereof.

Referring now to the drawings, in which like reference numerals represent like parts throughout the views, FIG. 1 shows a plan view of a pad or mattress designated generally by reference numeral 10. The pad or mattress 10 of regular size consists of a cover 12 covering, according to the preferred embodiment, a single layer of beads 14. The beads 14, forming the mattress body, are linked up together by threads or strings 16 to prevent displacement thereof.

Figure 2:
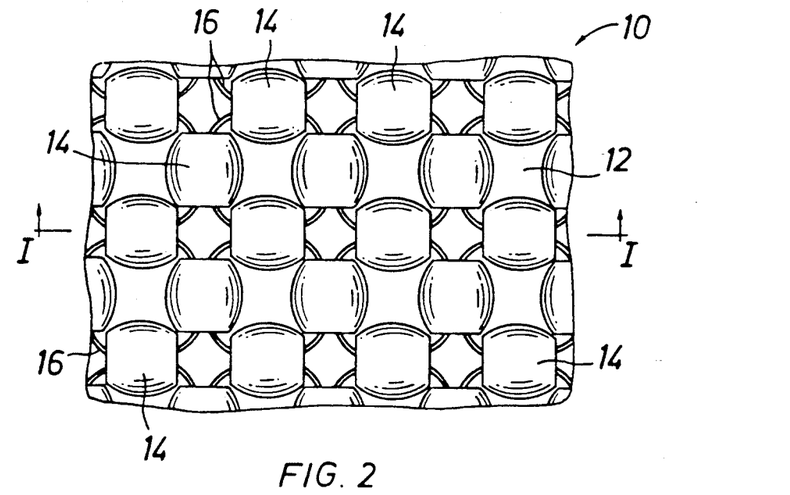
FIG. 2 is an enlarged fragmentary plan view of a layer of barrel-shaped beads.

FIG. 2 is an enlarged plan view of the mattress 10 depicting detailed construction of the layer of beads 14. Each of the beads 14 is, according to the present embodiment, generally barrel-shaped having a through hole 18.

The beads 14 are arranged diagonally with respect to one another. The through holes 18 (see FIGS. 3a to 3d) of a row of beads 14 are longitudinally disposed whilst the through holes 18 of the adjacent row of beads 14 are latitudinally disposed as illustrated in FIG. 2.

Although the beads 14 have been described as being arranged in diagonal relationship, it is understood that they may be arranged in orthogonal, irregular, or other relationships without departing from the scope of the present invention.

Figure 3A:
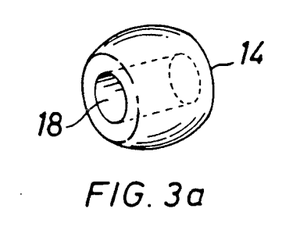
FIG. 3a is a barrel-shaped bead according to the embodiment in FIG. 2.

FIG. 3a is a perspective view of the barrel-shaped bead 14 shown in FIG. 2. The bead 14 has a longitudinally extending through hole 18.

Figure 3B:
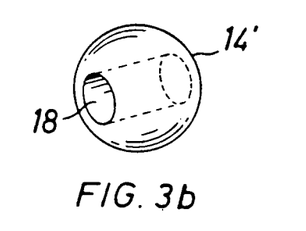
FIG. 3b is a second embodiment of the bead in a spherical configuration.
Figure 3C:
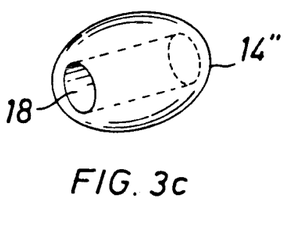
FIG. 3c is a third embodiment of the bead in an oval or generally elongated configuration.
Figure 3D:
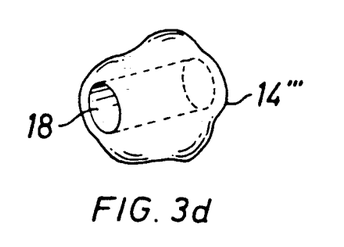
FIG. 3d is a fourth embodiment of the bead in an irregular configuration.

The beads 14 may be of other configuration as shown in FIGS. 3b, 3c and 3d. The pad or mattress 10 may consist of spherical beads 14', elongated or oval beads 14'', beads 14''', of irregular shape, or a combination thereof. The size of beads 14, 14', 14'', 14''' may vary and, preferably, in the region of 5 mm–40 mm in dimension.

Figure 4:
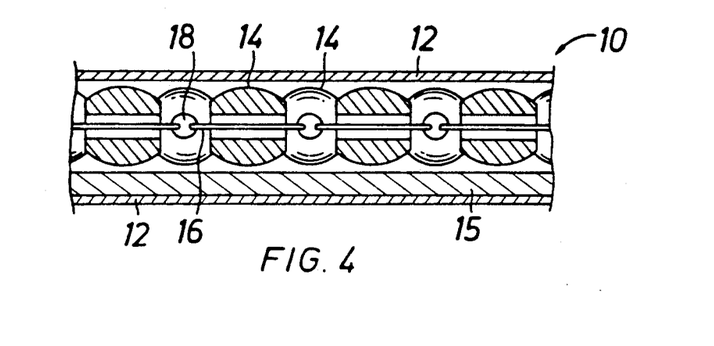
FIG. 4 is a sectional view of the layer of beads taken generally along line I—I of FIG. 2.

FIG. 4 shows a sectional view of the mattress 10 in accordance with the embodiment shown in FIG. 2. It can be seen that the beads 14 are linked up together forming a unitary layer of mattress. A bedding layer 15 of foam rubber or other resilient material is located beneath the layer of beads 14 in order to produce a cushioning effect. This foam rubber bedding preferably has a thickness of 1.2 cm to 5.0 cm.

The mattress cover 12, preferably fabricated from cloth, or thin foam rubber, or other desirable materials, serves to cover the layer of beads 14 and give a clean and comfortable outlook for the mattress 10.

The strings 16 are made of a flexible and high tensile material, such as thread, nylon, or steel wire so as to hold the beads 14 in a fixed position with respect to one another. The beads 14 are made of a relatively hard material such as wood, plastic, or rubber. The mattress 10 is therefore given good characteristics by means of relatively inexpensive materials.

Figure 5:
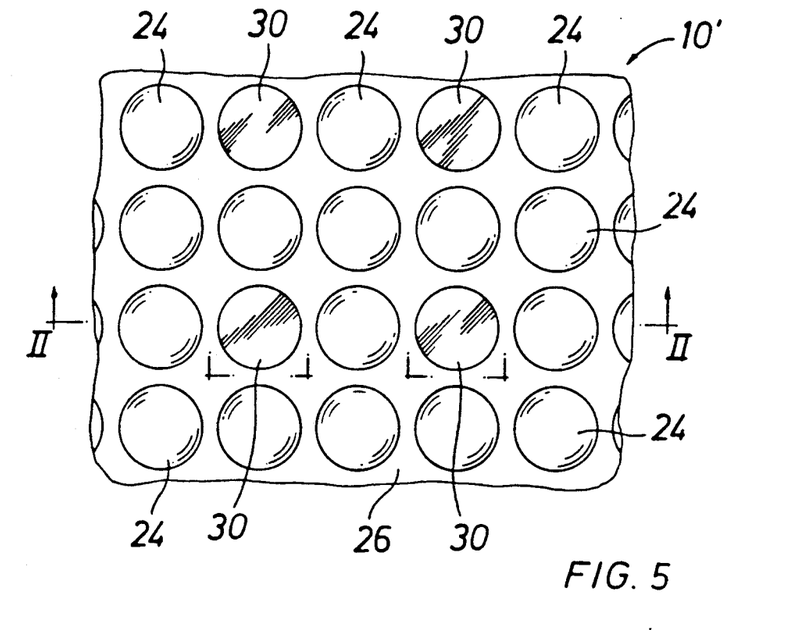
FIG. 5 is an enlarged fragmentary plan view of another embodiment of the layer of beads.
Figure 6:
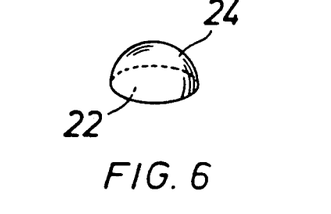
FIG. 6 is a semispherical bead without a through hole in accordance with the embodiment of FIG. 5.

FIG. 5 shows an enlarged plan view of a second embodiment of the pad or mattress of the present invention which is generally represented by reference numeral 10'. According to this preferred embodiment, beads 24 are secured to a sheet member 26 to form the mattress body. According to the preferred embodiment, each of the beads 24 is semispherical in shape and has no through hole provided thereon, as shown in FIG. 6. A substantially flat bottom surface 22 is provided on each of the beads 24 and is adapted to be seated on the upper surface of the sheet member 26.

The beads 24 are preferably adhered to the sheet member 26 by adhesive means such as glue. The beads 24 may also be secured to the sheet member 26 by other conventional means. According to the embodiment shown in FIG. 5, the beads are arranged in orthogonal relationship with one another. This permits automation of the manufacturing process.

The beads 24 are preferably made of wood, plastic, or rubber. The sheet member, serving as a base of the mattress body, is made of a flexible material such as a piece of cloth of strong fiber, or nylon, or other suitable materials.

Alternatively, the beads 24 may also be provided integrally with hole or holes to allow the beads to be threaded to the sheet member 26.

A cover 28 is used to cover the mattress body to provide a comfortable and clean exterior to the mattress 10'.

Figure 7:
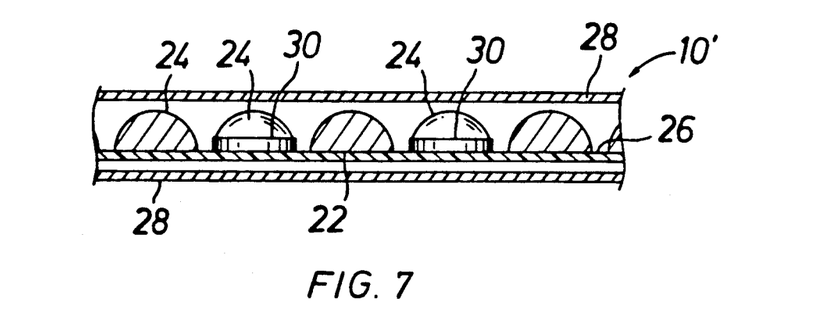
FIG. 7 is a sectional view of the layer of beads taken generally along line II—II of FIG. 5.

FIG. 7 is a sectional view of the mattress 10' in accordance with the embodiment shown in FIG. 5. It can be seen that the beads 24 are disposed in a spaced relationship with one another. This renders the mattress 10' to be in a good ventilating condition and allows the mattress 10' to be rolled up for storage.

This beads-and-sheet construction is more flexible in the sense that the beads 24 can be attached to the sheet member 26 in any pattern. Furthermore, mass production of the mattress 10' is made feasible.

The mattress 10 or 10' of the present invention may further be provided with magnetic devices such as magnets of an appropriate magnetic flux density. As illustrated in FIGS. 5 and 7, magnets 30 are in the shape of a disk and are generally positioned between and among the beads 24. These magnets 30 are provided and secured at the regions of the mattress 10' which come into close contact with the body of the user. Magnets may also be mounted on the mattress 10 by string means or other suitable means. These magnets act further to manipulate the body of the user for remedial purposes.

The magnetic force generated from the magnets has a healing effect on users suffering from fatigue. It releases the user from pain in the spinal cord, waist and other parts of the body. It also eases stiff shoulders of the user. The magnetic force also adjusts the functions of the human organs of the user.

Figure 8:
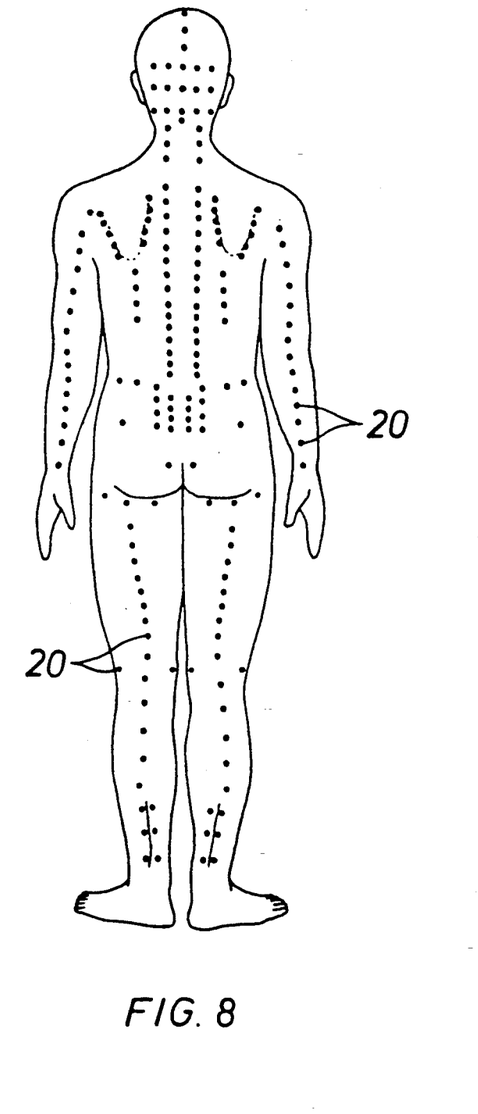
FIG. 8 is an illustrative diagram showing the pressure points located on the back of the human body.

When a user lies on the mattress 10 or 10' during treatment, the layer of beads 14 or 24, defining an array of pressure points, uniformly support the body of the user and apply pressure at a number of points on the back of the body. This gives rise to a similar effect of a treatment of finger massage or massage by means of an electrical massage apparatus. The points on the back of the body known to respond to pressure are indicated by reference numeral 20 shown in FIG. 8.

These points are held to correspond with specific organs of the human body. When they are stimulated, the corresponding organs are being treated and respond to the stimulation.

It is believed that vital energy flows constantly throughout the human body. According to the Chinese conception, this vital energy is made up of a balance mixture of the Yin and Yang. This is the continuous flow of this vital energy both over the entire surface of the body and along the special lines or channels which correspond with the major organs within the human body. Some of these lines or channels, which are called meridians in the West, correspond with the heart, liver, spleen, lungs, kidneys, and others with the large and small intestines, stomach, bile ducts and the bladder.

For the relief from many diseases and pains occurring in various parts of the body, the apparatus of the present invention is at least as effective as the ingestion of medical remedies. In helping to promote blood and vital energy circulation, the apparatus speeds up the metabolism of the body and can help cure diseases and pains including lumbago, sciatica, insomnia, constipation, hypertension, headache, knee pain, back pain, and stiff neck and shoulders.

Figure 9:
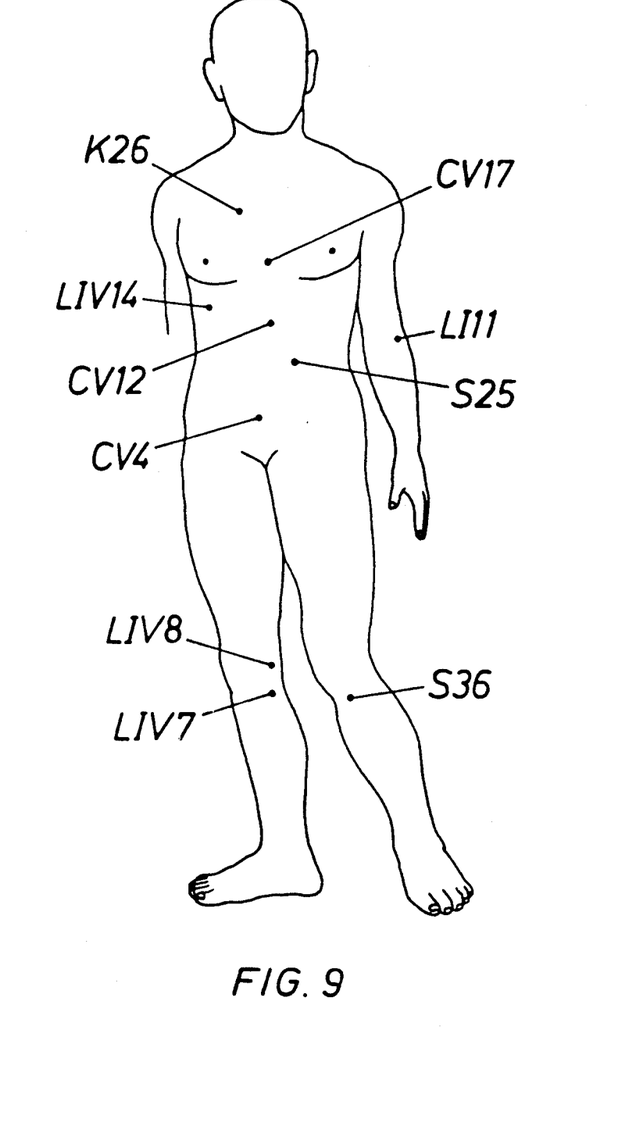
FIG. 9 is an illustrative diagram showing some commonly used acupuncture points located at the front of the human body.
Figure 10:
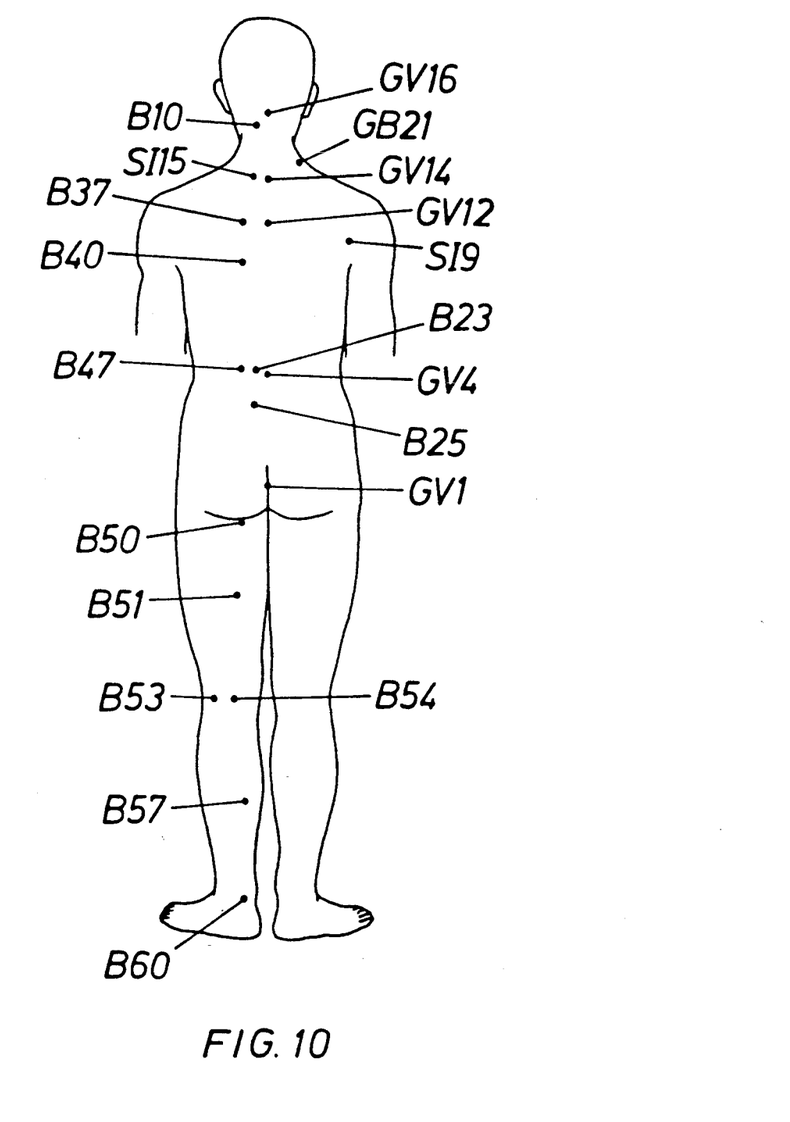
FIG. 10 is an illustrative diagram showing some commonly used acupuncture points located on the back of the human body.
Figure 11:
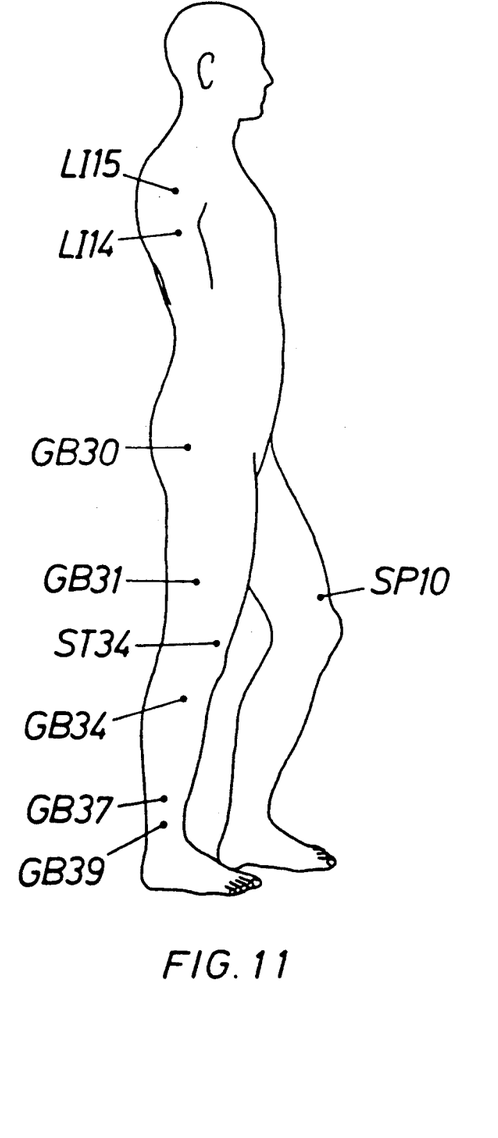
FIG. 11 is an illustrative diagram showing some commonly used acupuncture points located on the side of the human body.

Some of the points used for treatment of the human body are indicated in FIGS. 9, 10 and 11.

These points and their names and corresponding indications are listed as follows:

| Point | Name | Indication |
| --- | --- | --- |
| B10 | Tienchu | Stiff neck, Neurasthenia, Hysteria, Headache. |
| B23 | Shenshu | Lumbago, Impotence. |
| B25 | Tachangshu | Constipation, Lumbago. |
| B37 | Pohu | Sciatica, Hemiplegia. |
| B40 | Yihsi | Sciatica. |
| B47 | Chihshih | Lumbago, Impotence, Dysuria. |
| B50 | Chengfu | Neuralgia in the limbs. |
| B51 | Yinmen | Sciatica, Hemiplegia. |
| B53 | Weiyang | Ankle dullness and pain. |
| B54 | Weichung | Sciatica, Hemiplegia. |
| B57 | Chengshan | Gastrocnemius muscle cramp, Leg pain. |
| B60 | Kunlun | Sciatica, Hemiplegia. |
| CV4 | Kuanyuan | Dysmenorrhoea, Impotence, Diarrhoea. |
| CV12 | Chungwan | Gastroptosis, Nausea, Stomach diseases |
| CV17 | Shanchung | Mental strain. |
| GB21 | Chienchin | Shoulder pain. |
| GB30 | Huantiao | Lumbago, Sciatica. |
| GB31 | Fengshih | Paralysis of the legs. |
| GB34 | Yanglingchuan | Cholecystitis, Hemiplegia, Liver and gall-bladder diseases. |
| GB37 | Kuangming | Blurred vision. |
| GB39 | Hsuanchung | Ankle joint pain. |
| GV1 | Changchiang | Hemorrhoids. |
| GV4 | Mingmen | Lumbago, Impotence. |
| GV12 | Shenchu | Mental strain, Insomnia. |
| GV14 | Tachui | Back pain, Stiff neck. |
| GV16 | Fengfu | Headache, Stiff neck, Apoplexy. |
| K26 | Yuchung | Bronchitis. |
| LI11 | Chuchih | Hypertension, Paralysis, Elbow pain. |
| LI14 | Pinao | Arm pain, Hemiplegia. |
| LI15 | Chienyu | Frozen shoulder, Hemiplegia. |
| LIV7 | Hsikuan | Arthritis of the knee. |
| LIV8 | Chuchuan | Arthritis of the knee. |
| LIV14 | Chimen | Diabetes, Mental strain. |
| S25 | Tienshu | Acute or chronic gastro-enteritis, Distension of the abdomen. |
| S34 | Liangchiu | Knee weakness and pain, Gastric pain. |
| S36 | Tsusanli | Indigestion, Diabetes, Vomiting. |
| SI9 | Chienchen | Shoulder pain, Tinnitus. |
| SI15 | Chienchungshu | Insomnia, Lumbago. |
| SP10 | Hsuehhai | Thigh pain, Menorrhagia. |

The mattress 10 or 10' is relatively thin and light in weight as compared with conventional, bulky spring mattress. The beads-and-string construction and the beads-and-sheet construction render the mattress 10 or 10' to be very flexible and, as such, can be rolled up for easy storage and transportation.

Due to the fact that a lot of space is provided between the beads 14 or 24, the mattresses 10 and 10' of the present invention have a good ventilating property. Thus, inhibition of respiration of the skin of the body and undesirable rise in body temperature can be minimized and a sound sleep can be guaranteed.

Although the layer of beads has been described herein before as being a mattress, it is contemplated that the layer of beads may be incorporated for other purposes. For example, the layer of beads may be incorporated to a seating or a floor mat.

Figure 12:
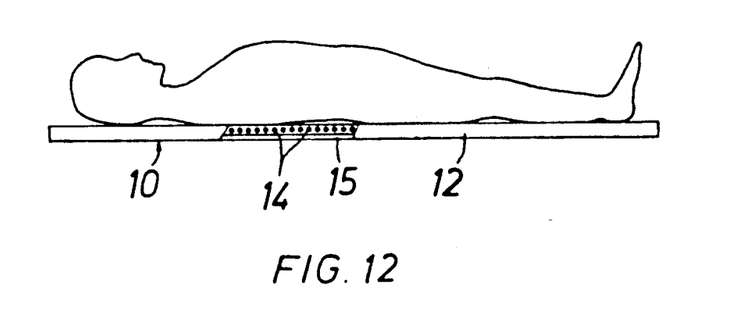
FIG. 12 is an explanatory diagram showing a human subject using a massage apparatus of the present invention which serves as a mattress.
Figure 13:
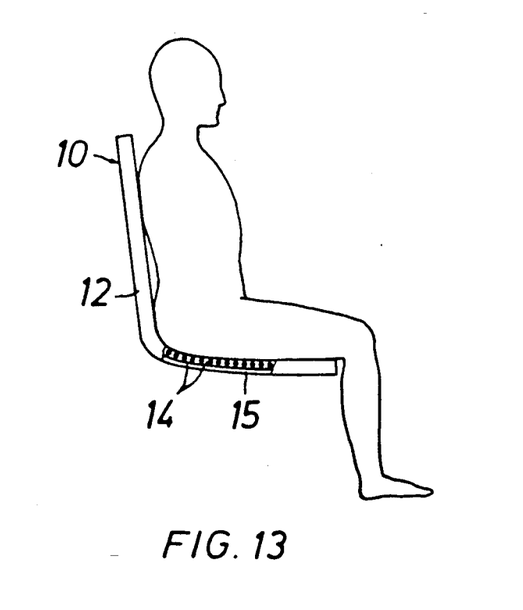
FIG. 13 is an explanatory diagram showing a human subject using a massage apparatus of the present invention which serves as a seating cushion.

FIGS. 12 and 13 are explanatory diagrams showing the layer of beads being used as a mattress and a seating cushion respectively.

While the present invention has been shown and described with particular reference to a preferred embodiment thereof, it should be noted that various other changes and modifications may be made without departing from the scope of the present invention.

I claim:

1. A human body support apparatus for sitting and sleeping, comprising:

a layer of hardwood or plastic beads closely spaced together to become a fixed array of pressure points for the application of pressure to parts of the human body;

a cushioning layer positioned beneath the layer of beads to provide a restoring force with cushioning effect to the hard beads;

an upper cover layer overlying the layers of beads;

a lower cover layer positioned beneath said cushioning layer;

said beads each having a hole through it which is substantially centrally located, said bead layer including a first group of spaced parallel rows, with the holes of the beads of each row being axially aligned and the beads axially spaced, said bead layer including a second group of spaced parallel rows of beads with the beads in each row of said second group having its holes axially aligned and with the axes of the holes of said second group of rows extending substantially perpendicular to the hole axes of the first group of rows, the beads in the rows of the second group being axially spaced from each other, the rows of beads being arranged so that a space is located on each side of each bead, and a bead is located on each side of each space; and a line extending through the holes in said beads to connect said beads in said fixed array.

2. The apparatus of claim 1, comprising a plurality of magnetic disks adjacent to said beads.

* * * * *